United States Patent [19]

Ricci

[11] Patent Number: 5,420,018

[45] Date of Patent: May 30, 1995

[54] DEVICE FOR THE PRESERVATION AND ANALYSIS OF SAMPLES, IN PARTICULAR FOR BACTERIOLOGICAL EXAMINATIONS, ISOLATION OF MICRO-ORGANISMS AND DEVELOPMENT OF ISOLATION COLONIES, AND A METHOD FOR SEEDING THE SAMPLES ONTO A CULTURE MEDIUM IN SAID DEVICE

[75] Inventor: Antonio Ricci, Monteriggioni, Italy

[73] Assignee: Diesse Diagnostica Senese S.r.l., Milan, Italy

[21] Appl. No.: 85,195

[22] Filed: Jun. 29, 1993

[30] Foreign Application Priority Data

Jul. 8, 1992 [IT] Italy .................. MI92U0678

[51] Int. Cl.⁶ .................... C12Q 1/24; C12M 1/24
[52] U.S. Cl. ................... 435/30; 435/292; 435/293; 435/294; 435/295; 435/296; 435/297
[58] Field of Search ............ 435/30, 292, 294, 296, 435/293, 295, 297

[56] References Cited

U.S. PATENT DOCUMENTS

| | | | |
|---|---|---|---|
| 3,589,983 | 6/1971 | Holderith et al. | 435/30 |
| 4,308,347 | 12/1981 | Forrer et al. | 435/34 |
| 4,801,547 | 1/1989 | Rosenberg | 435/292 |
| 4,859,586 | 8/1989 | Eisenberg et al. | 435/34 |

FOREIGN PATENT DOCUMENTS

| | | |
|---|---|---|
| 0428909 | 5/1991 | European Pat. Off. . |
| 2348269 | 11/1977 | France . |
| 2612297 | 9/1988 | France . |

*Primary Examiner*—Irene Marx
*Attorney, Agent, or Firm*—Steinberg, Raskin & Davidson

[57] ABSTRACT

A device for the preservation and analysis of samples, comprising a first container (1) and a second container (5) for containing a sample and a maintaining or culture liquid; said first container comprises at least two mutually communicating chambers (2, 3), of which a first chamber (2) comprises an element (7) carrying a culture medium and a distributor member (19), and the second chamber (3) comprises on its base (13) at least one element (14) projecting into the chamber itself and able to break at least one weakened portion (26) of the base (SA) of said second container (5), this latter being insertable into said second chamber (3).

The method for seeding onto the face of the element (7) comprises distribution along paths extending substantially in mutually perpendicular directions which are preferably parallel and, respectively, orthogonal to the axis of the element (7).

18 Claims, 3 Drawing Sheets

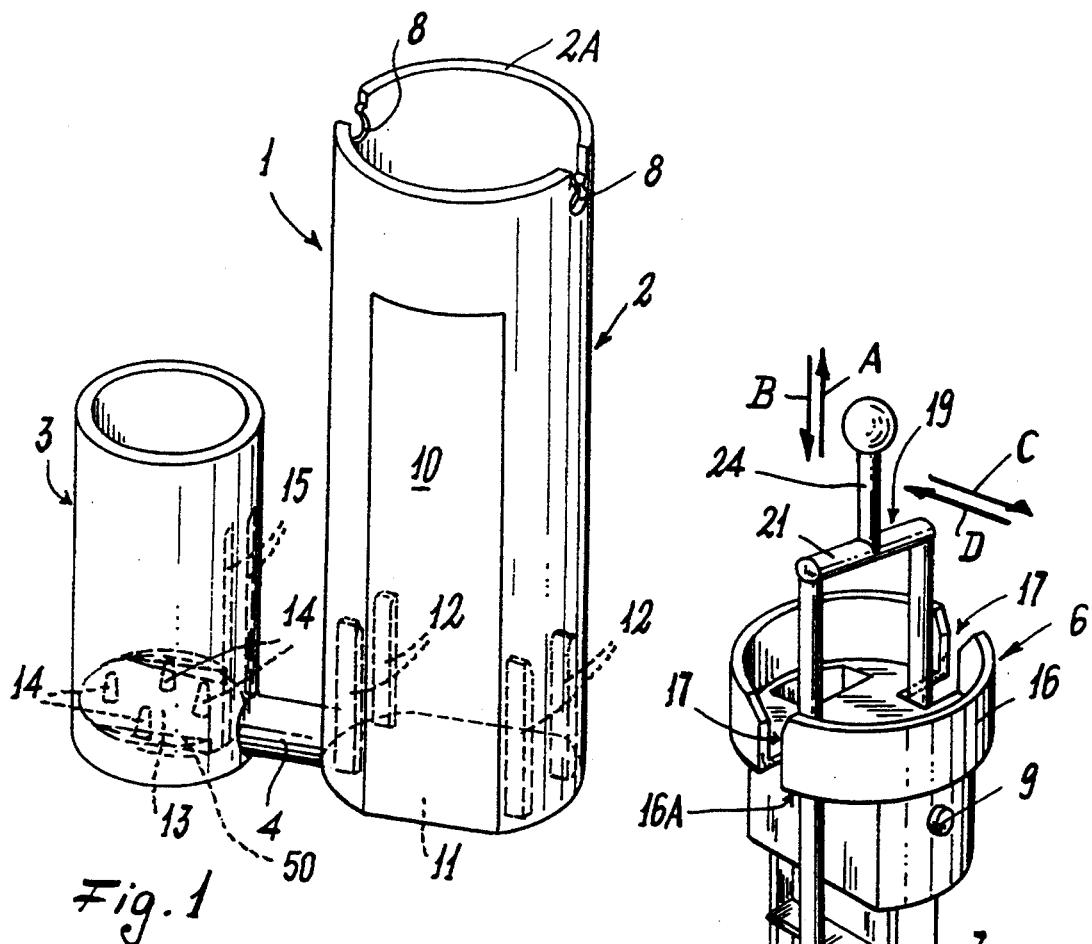
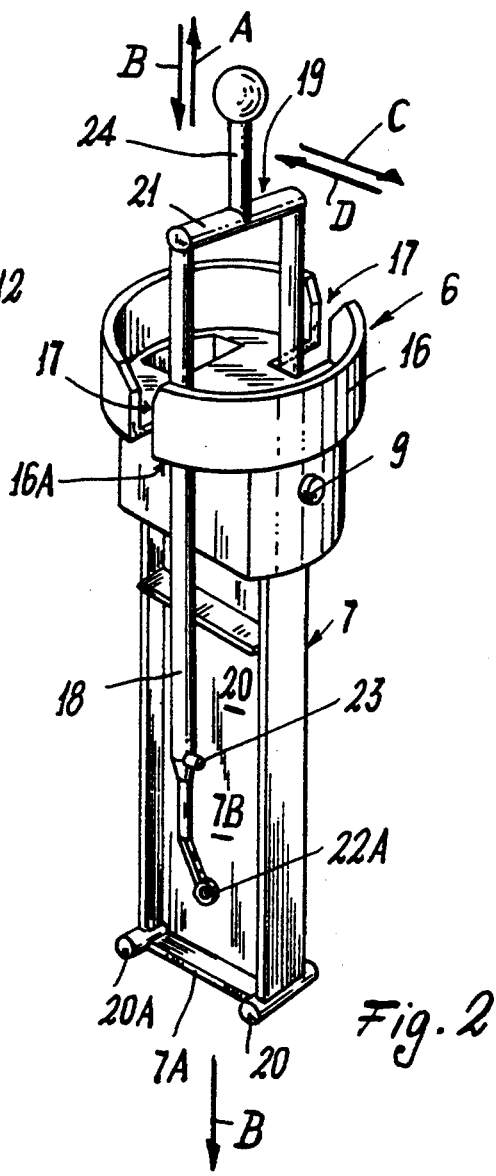
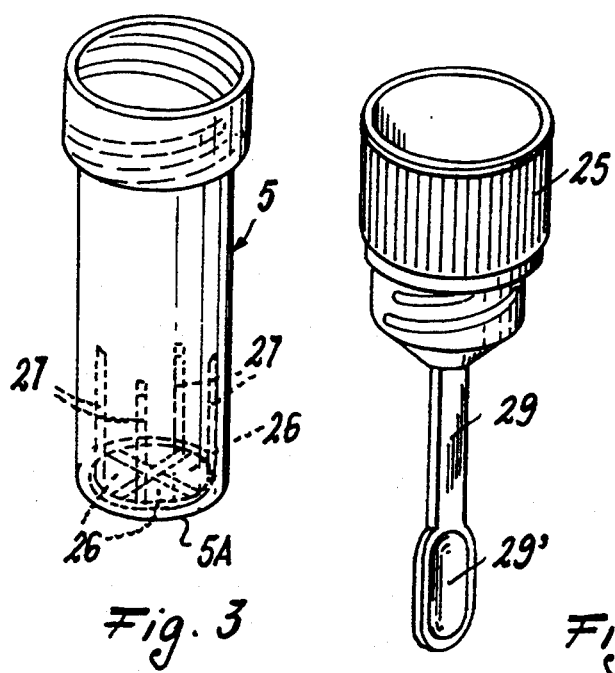

DEVICE FOR THE PRESERVATION AND ANALYSIS OF SAMPLES, IN PARTICULAR FOR BACTERIOLOGICAL EXAMINATIONS, ISOLATION OF MICRO-ORGANISMS AND DEVELOPMENT OF ISOLATION COLONIES, AND A METHOD FOR SEEDING THE SAMPLES ONTO A CULTURE MEDIUM IN SAID DEVICE

BACKGROUND OF THE INVENTION

This invention relates to a device for the preservation of samples in particular for bacteriological examinations, isolation of micro-organisms and development of isolation colonies, of the type comprising an element carrying at least one selective culture medium and insertable into a first container, and a distributor member slidable with slight contact along said selective culture medium, and to a method for seeding the samples onto said culture medium.

Various devices of the aforesaid type are known (see for example U.S. Pat. Nos. 3,589,983, 4,801,567 and 4,859,586). In known devices, in order to effect the desired examination if is always necessary for a laboratory analyst to place the sample to be analyzed, and/or the biological development liquid in which said sample is immersed, into the container containing the element provided with the culture medium.

Examples of such samples are feces, urine, excretion, nasal or ear swabs, and other materials withdrawn for diagnostic purposes.

The operations involved in filling the container present considerable drawbacks.

In this respect the laboratory analyst can easily come into contact with such samples, with possible serious risk to his health.

In addition, the samples often emit a bad odour, which is inhaled by the laboratory analyst during the filling operations.

The laboratory analyst then seeds the sample on the culture medium using the distributor member.

In known devices this seeding can only be achieved substantially vertically, parallel to the major axis of the culture medium.

OBJECTS AND SUMMARY OF THE INVENTION

An object of the present invention is to provide a device of the aforesaid type which enables the sample for examination to be transferred into the container housing an element loaded with one or more culture media without the laboratory analyst who makes this transfer undergoing any risk of contact with the sample or of. inhaling the effluvia emitted thereby.

A further object is to provide a device of reliable and safe operation andof low cost.

A further object is to develop a seeding method which enables the sample to be distributed on the culture medium using movements which are not limited to a single direction.

These and further objects which will be apparent to the expert of the art are attained by a device in accordance with the accompanying claims.

The present invention will be more apparent from the accompanying drawings, which are provided by way of non-limiting example and in which:

BRIEF DESCRIPTION OF THE DRAWINGS

FIG. 1 is a perspective view of a first container of a device according to the invention;

FIG. 2 is a perspective view to a scale greater than FIG. 1 showing a stopper for the larger-dimension chamber of the first container;

FIG. 3 is a perspective view of a second container of a device according to the invention;

FIG. 4 is a perspective view of a stopper for the second container;

DETAILED DESCRIPTION OF THE INVENTION

Figure 5:
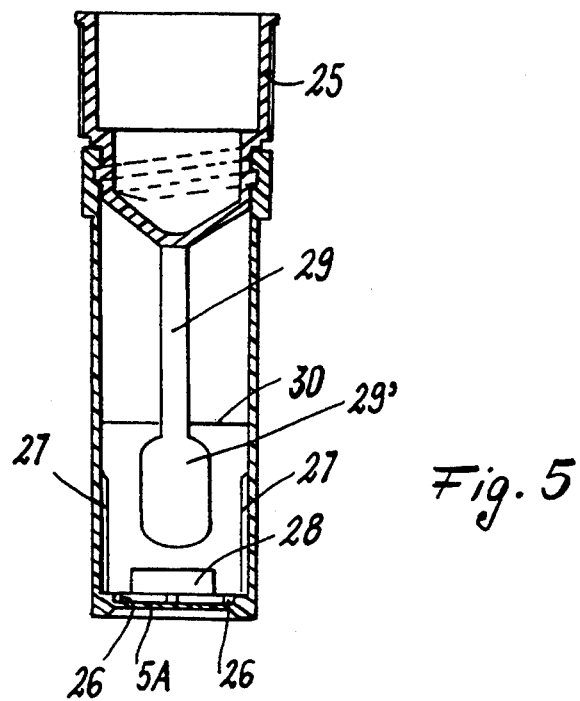
FIG. 5 is a longitudinal section through the second container.

With reference to said figures, the device of the invention comprises a first container (FIG. 1) with two substantially cylindrical chambers 2 and 3 communicating with each other via a base duct 4, a second container 5 with a cap (FIG. 3), and a stopper 6.

The two cylindrical chambers 2 and 3 of the first container are preferably of different dimensions; the larger-dimension chamber 2 can be closed by the stopper 6 to house the elongate element 7 which extends from the stopper to which it is connected, while the smaller-dimension chamber 3 can receive the second container 5.

More specifically, in its upper edge the larger-dimension chamber 2 comprises means 8 for snap, fitting the stopper 6; in the illustrated embodiment these means are slots 8 shaped to be copenetrated snapwise by opposing prongs 9 (only one of which is visible in FIG. 2) provided on the lateral surface of the stopper 6.

On its lateral surface the chamber 2 comprises two opposing flat portions 10 which, as described hereinafter, enable the element 7 to be viewed from the outside when inserted into the chamber. Finally, extending from its base 11, the chamber 2 comprises guide elements 12 in the form of internal ribs for guiding the end part 7A of the elongate element 7 associated with the stopper 6. The guides 12 are arranged such that the flat faces 7B of the element 7 face the flat portions 10 of the chamber wall.

The smaller-dimension chamber 3 comprises on its base 13 a plurality of pointed projections 14 (four in the illustrated embodiment) and, along its inner lateral surface and nearly as far as the base, two longitudinal portions 15 slightly projecting from the surface and arranged to retain the container 5 when this is inserted into the chamber 3.

The base 13 of the chamber 3 is advantageously inclined towards the second chamber 2 so that a liquid present in the chamber 3 can flow through the duct and into the larger-dimension chamber 2.

Spacers 50 are also provided on the base 13 of the chamber 3 to maintain the container 5 spaced from the base 13 when, as described hereinafter, the container 5 is pushed into the chamber 3 to break the base 5A of the container 5.

The stopper 6 comprises substantially two parts connected together, namely a cylindrical part 16 the lower edge 16A of which abuts against the free edge 2A (FIG.

1) of the chamber 2 of the container 1, and a substantially parallelepiped elongate element 7 which is to be inserted into said chamber 2.

More specifically, the cylindrical part 16 is internally hollow and comprises two diametrically opposing slots 17 for passage of the arms 18 of a fork-shaped seeding or distributor member 19. The elongate part 7 comprises in each of its larger-dimension faces a recessed seat 20 for containing suitable known solid culture media (the culture medium is not shown but is of conventional type). In proximity to the end part 7A of the elongate element 7 there are provided, in correspondence with the smaller-dimension walls, prongs 20A to engage in the guides 12 provided in the chamber 2.

At their ends, the arms 18 of the fork 19 comprise seeding loops or needles 2 (a single loop is provided with each arm in the illustrated embodiment, however a plurality of loops or similar elements can be associated with its end). Advantageously, said seeding loops are inclined to the axis of the arms 18 so that on raising the fork, the end 22A of said loops touches the culture medium provided on the faces 7B of the element 7.

In proximity to each of the lower ends of the arms 18 of the seeding fork 19 there is advantageously provided a prong 23 to prevent accidental extraction of the fork from the stopper 6. In this respect, if the fork is raised the prongs 23 abut against the lower edge 16A of the cylindrical part 16 of the stopper 6.

The upper ends of the fork arms 18 are connected together by a cross-member 21 from which an operating arm 24 extends.

The fork is dimensioned so that when the stopper 6 closes the chamber 2 of the container 1, the ends 22A of the seeding loops 22 are in proximity to the base 11 of said chamber.

By means of the operating arm 24, the fork can be moved vertically (in the direction of the arrows A and B of FIG. 2) and also horizontally (in the direction of the arrows C and D of FIG. 2) so that the ends 22A of the seeding loops can be moved from the base of the chamber 2 and onto the culture medium provided on the faces 7B of the element 7.

It should be noted that the arms 18 of the fork 19 are able to undergo rotary and lifting movement by virtue of the apertures 17 provided in the stopper 6.

The second container 5, of substantially cylindrical shape, comprises in its upper edge a threaded part allowing a cap 25 to be screwed to the container, and comprises weakened portions 26 in its base 5A. Stiffening ribs 27 are preferably provided along the inner walls of the container, in proximity to the base 5A. On the base of the container there rests a magnetic armature 28 (FIG. 5) for stirring a usual maintaining or culture liquid provided in the container (the level of which is indicated by 30 in FIG. 5).

With the cap 25 there is associated a spatula 29 the end part 29' of which, when the cap is mounted on the container 5, is immersed in the maintaining or culture liquid present in the container (see FIG. 5).

The spatula 29 allows a feces sample to be taken. If other types of samples such as urine, blood or excretions are to be taken, the spatula is replaced by usual known elements for taking the sample and transferring it into the maintaining liquid.

If a urine or blood sample is to be taken, a conventional dropper (not shown) can be associated with the cap 25.

Alternatively, if blood, urine or other similar liquid samples are to be taken, the container 5 can be evacuated of air by known procedures, for example of the type used for test-tubes for collecting blood samples by vacuum systems. In this case the container 5 comprises a usual plug, for example of rubber, of the type provided in said test-tubes, and the urine or blood sample is drain into the container 5 by a known holder with needle, also of a type similar to those used for taking blood samples by vacuum systems.

In the case of other body fluids, for example excretions or miscellaneous swabs, the spatula 29 is replaced by an element, such as a needle, able to retain a cotton or gauze flock to be introduced into the biological development or maintaining liquid.

All the components of the device are preferably constructed of plastics material by moulding. The chambers 2 and 3 and the container 5 are advantageously transparent.

Figure 6:
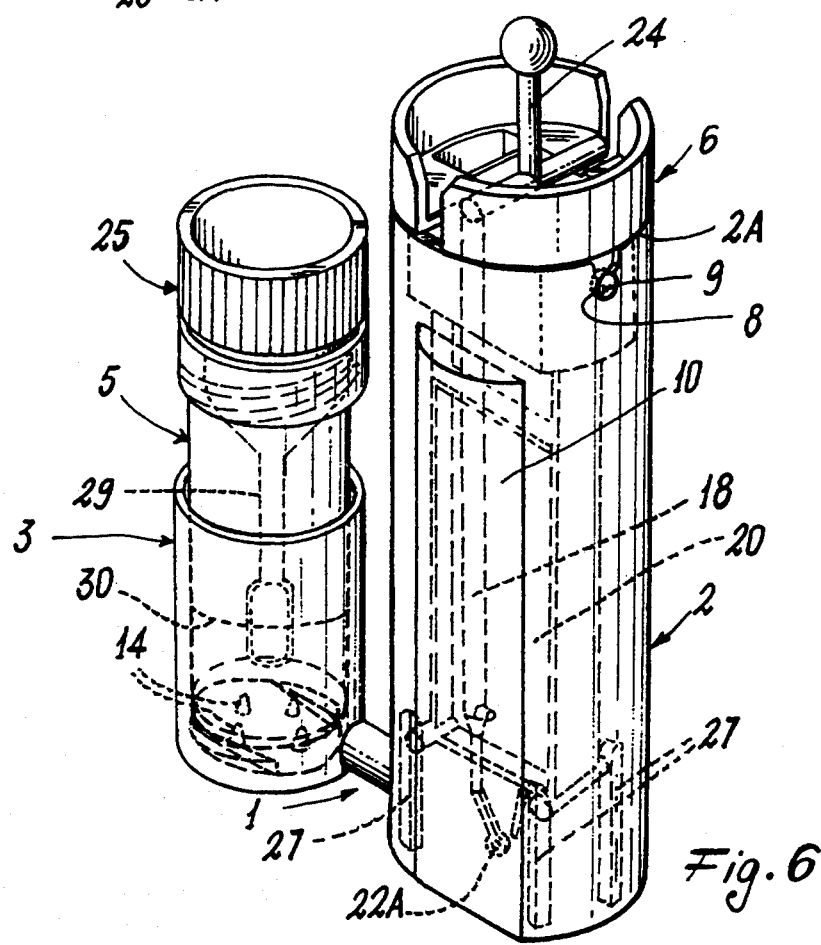
FIG. 6 is a perspective view of the device according to the invention.

If the device of the invention is to be used for feces analysis, the patient picks up a sample of feces with the spatula 29 and by screwing the cap 25 onto the container 5 inserts the spatula into the maintaining or culture broth contained in the container. This latter is then transferred to, an analysis laboratory where it can be inserted into a known machine which, by means of a magnetic stirrer, moves the magnetic armature present in the sample container to homogenize the faces in the culture broth. The laboratory analyst then inserts the second container 5, containing the sample, into the chamber 3 of the first container (see FIG. 6) and presses it within this latter so that the projections 14 break the base of the sample container. In this manner culture liquid or broth passes through the duct 4 and into the first chamber 2 so as to graze the ends 22A of the seeding needles 22.

The container 1 is then maintained at a temperature of 35° C. for the time required for the germs of interest to develop within the culture broth (generally 12-24 hours).

By moving the fork 19 in the direction of the arrows A, B, C, D (FIG. 2) the seeding loops 22 wetted with culture broth and containing germs are passed over the solid culture media provided on the faces 7B of the elongate element 7. By varying the movements of the forks 19 the said culture media can be seeded to different concentrations and in different ways as described hereinafter.

The culture media can be of different types, known to the expert of the art, depending on the: required microbie selection test.

After the microbie development on the culture media the laboratory analyst withdraws the possible suspect colony for the subsequent identification tests.

All the aforesaid operations can also be effected in succession automatically.

It should also be noted that with the device of the invention numerous ways of seeding germ-containing culture broth onto the culture medium are possible, and in particular the broth can be seeded in specific determined ways depending on the type of examination to be carried out.

Figure 7:
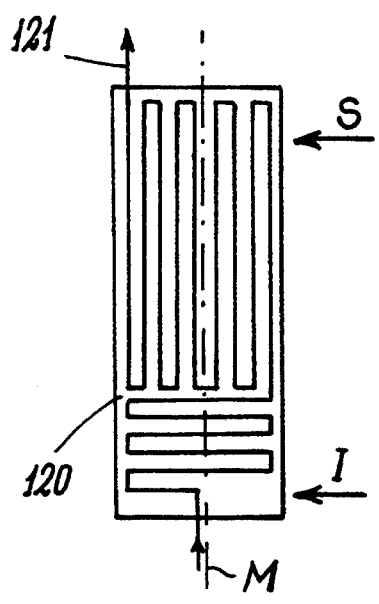
FIGS. 7 and 8 show two particular types of characteristic seeding path for examining faces and urine respectively.

FIG. 7 shows a culture medium 120 and a possible preferred seeding path 121 for effecting a feces examination. In this type of examination it is important that the seeding path of the loops 22 of the fork 19 along the culture medium 120 be as extensive as possible to facilitate isolation of the colonies. With a seeding path of the type shown in FIG. 7 the colonies can be easily isolated whatever the bacterial loading of the broth. In this respect, if there is high bacterial loading in proximity to the lower end I of the culture medium 120 there are a large number of colonies and these fare difficult to isolate, whereas in proximity to the upper end S the colonies have thinned out and are easy to isolate. In contrast, in the case of low bacterial loading of the broth, the easily isolated colonies are at the lower end I of the culture medium 120 whereas at the upper end S the colonies do not develop.

Figure 8:
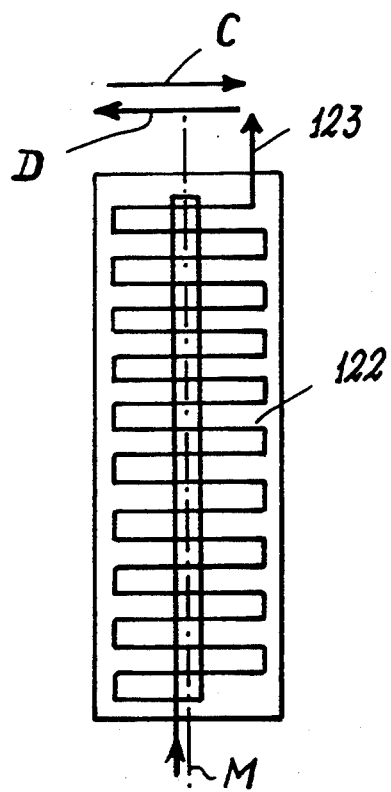

FIG. 8 shows a culture medium 122 for effecting a urine examination. In this type of examination, in addition to bacterial isolation it is also necessary to count the germs present in the broth in order to be able to establish whether there is any infection of the urinary tracts.

In this type of examination a broth can be considered pathological even if it contains a bacterial load which is not very high (for example 100,000 germs per milliliter), and the broth is therefore seeded homogeneously on the culture medium so as to facilitate both the bacterial count and the isolation.

In this respect, the broth is advantageously initially seeded along the major axis (M) of the culture medium 122, after which it is extended over the entire culture medium 122 in a direction perpendicular to the major axis H.

From the aforegoing examples it is apparent that the seeding device allows easy movement of the fork 19 parallel to the major axis M of the culture medium and/or perpendicular and/or in an inclined direction thereto.

This movement of the fork is preferably effected mechanically in an automatic manner, but can also be effected manually.

The proposed arrangement has considerable advantages over the conventional system in that:

1) the patient, or the person acting for him, directly takes the sample and limits the volume to the quantity necessary for the examination, so that the laboratory analyst is not required to withdraw the necessary quantity from an excessive amount of sample, as generally currently happens;

2) because of the presence of the second container 5 for the enrichment broth the sample preserves the germs contained in it for a certain time, so that the subsequent examination, such as the isolation or counting of the germs, is without doubt more accurate, and the time for delivering the sample to the laboratory can be extended;

3) the laboratory analyst never comes into contact with the sample, so eliminating an occurrence which is both unpleasant and dangerous for contamination. In this respect, the container for the sample to be analyzed is never opened by the laboratory analyst, who merely places it in the chamber 3;

4) isolation is achieved in a shorter time;

5) the broth can be seeded on the culture medium in an optimum and specific manner for the examination to be effected.

Finally, it should be noted that the described embodiment is provided by way of non-limiting example, and that numerous modifications are possible, all falling within the scope of the inventive concept.

I claim:

1. A device for the storage and analysis of samples for bacteriological examinations, isolation of microorganisms and development of isolation colonies, comprising a first member supporting at least one solid culture medium, a first container comprising means defining at least two separated, communicating chambers, said first member being insertable into a first one of said chambers, said means defining a second one of said chambers comprising a base, an inoculating or distributor member arranged in said first chamber to contact said solid culture medium, said distributor member being movable in directions longitudinal and transverse to said first member, a second container adapted to contain a sample and a liquid maintenance or culture medium, said second container being separate from said first container and comprising a base having at least one weakened, penetratable portion, said second container being insertable into said second chamber of said first container, and at least one projecting element arranged on said base of said second chamber of said first container, said projecting element being arranged to penetrate said at least one weakened portion of said base of said second container upon insertion of said second container into said second chamber of said first container such that said liquid maintenance or culture medium contained in said second container flows from said second chamber of said first container into said first chamber of said first container, and wets only a portion of said first member.

2. The device of claim 1, further comprising a stopper element engaging with said first chamber and being coupled to said first member and said distributor member.

3. The device of claim 1, wherein said distributor member has a fork shape, each of the arms (18) comprising at least one end element (22) able to retain and distribute on said solid culture medium at least part of the liquid present in said first chamber (2).

4. The device of claim 3, wherein said end elements (22) of the arms (18) of said distributor member (19) are inclined to said arms.

5. The device of claim 1, wherein said first chamber (2) has an interior and comprises guides (12) arranged in said interior for the insertion of said first member (7) carrying the culture medium.

6. The device of claim 1, wherein said first chamber has at least one transparent portion arranged opposite said first member.

7. The device of claim 1, wherein said second container (5) comprises a cap (25) with which at least one element (29) for retaining the sample to be examined is associated.

8. The device of claim 1, further comprising at least one projecting portion arranged on an inner surface of said second chamber, said at least one projecting portion arranged to improve the retention of said second container when it is inserted into said second chamber.

9. The device of claim 1, further comprising at least one stiffening rib arranged on an inner surface of said second container.

10. The device of claim 1, further comprising means for inducing the flow of a liquid present in said second chamber toward said first chamber and preventing flow of the liquid from said first chamber back to said second chamber, said means comprising an inclination provided in said base and a duct extending from said second chamber to said first chamber arranged in relation to said inclined base such that the liquid flows down the inclination into said duct.

11. The device of claim 1, further comprising at least one spacer element (50) arranged on said base of said second chamber, said at least one spacer element being arranged to maintain the second container spaced from said base (13) when inserted into said second chamber.

12. The device of claim 1, wherein said means defining said chambers comprise substantially cylindrical walls, said first and second container being substantially cylindrical and having peripheral corresponding dimensions to said first and second chambers, respectively.

13. The device of claim 1, further comprising means for sealing said first chamber, said sealing means being coupled to said distributor member such that said distributor member is movable when said first chamber is sealed.

14. The device of claim 2, said distributor member has an arm exterior to said first chamber, a cross-member connected to said arm, and a pair of arms connected to said cross-member and extending into an interior of said first chamber.

15. The device of claim 14, wherein said stopper has apertures through which said pair of arms of said distributor member extend such that upon lateral movement of said arm of said distributor member exterior to said first chamber, said pair of arms of said distributor member are rotatable.

16. A method for storing samples and inoculating the samples onto a culture medium for analysis, comprising the steps of:

supporting at least one solid culture medium in a first member, inserting the first member into a first chamber of a first container comprising at least two separate, communicating chambers, coupling an inoculating or distributor member to the first chamber to engage with the solid culture medium, placing the sample and a liquid maintenance or culture medium into a second container which is separate from the first container, inserting the second container into a second chamber of the first container such that at least one projecting element arranged on a base of the second chamber penetrates at least one weakened, penetratable portion of the second container causing the culture or maintaining liquid in the second container to flow from the second chamber into the first chamber and wet a portion of the distributor member, and inoculating the sample onto the solid culture medium by moving the distributor member both transversely and longitudinally to the culture medium.

17. The method of claim 16, further comprising the steps of: first inoculating the sample on at least part of the solid culture medium only longitudinally and then inoculating the sample onto the solid culture medium transversely.

18. The method of claim 16, further comprising the steps of inoculating the sample onto a first part of the solid culture medium only transversely, and then inoculating the sample onto a second part of the solid culture medium different from the first part only longitudinally.

* * * * *